United States Patent
Ahmed et al.

(10) Patent No.: US 11,385,217 B2
(45) Date of Patent: Jul. 12, 2022

(54) ONLINE MEASUREMENT OF DISPERSED OIL PHASE IN PRODUCED WATER

(71) Applicant: Saudi Arabian Oil Company, Dhahran (SA)

(72) Inventors: Elaf A. Ahmed, Dhahran (SA); Sebastien A. Duval, Dhahran (SA); Simone Less, Dhahran (SA); Ali S. Aldossary, Al Khubar (SA)

(73) Assignee: Saudi Arabian Oil Company, Dhahran (SA)

( * ) Notice: Subject to any disclaimer, the term of this patent is extended or adjusted under 35 U.S.C. 154(b) by 170 days.

(21) Appl. No.: 16/942,604

(22) Filed: Jul. 29, 2020

(65) Prior Publication Data

US 2022/0034863 A1     Feb. 3, 2022

(51) Int. Cl.
  *G01N 33/28* (2006.01)
  *B01D 17/02* (2006.01)
  *G01N 1/20* (2006.01)

(52) U.S. Cl.
  CPC ..... *G01N 33/2847* (2013.01); *B01D 17/0205* (2013.01); *G01N 1/2035* (2013.01); *G01N 2001/205* (2013.01)

(58) Field of Classification Search
  CPC ............. B01D 17/0205; G01N 1/2035; G01N 2001/205; G01N 33/1833; G01N 33/2847; G01N 33/26; G01N 33/22; G01N 33/28
  See application file for complete search history.

(56) References Cited

U.S. PATENT DOCUMENTS

| 2,825,026 A | 2/1958 | Holaday et al. |
| 3,778,706 A | 12/1973 | Thompson |

(Continued)

FOREIGN PATENT DOCUMENTS

| AU | 2004204512 | 7/2004 |
| CA | 2968601 | 6/2016 |

(Continued)

OTHER PUBLICATIONS

"Method 1664, revision A: N-Hexane extractable material (HEM; Oil and Grease) and silica gel treated n-hexane extractable material (SGT-HEM; Non-polar material) By extraction and gravimetry," United States Environmental Protection Agency, Office of Water, Washington D.C., EPA-821-R-98-002, PB99-121949, Feb. 1999, 28 pages.

(Continued)

*Primary Examiner* — John Fitzgerald
*Assistant Examiner* — Truong D Phan
(74) *Attorney, Agent, or Firm* — Fish & Richardson P.C.

(57) ABSTRACT

Online measurement of dispersed oil phase in produced water can be implemented a method on-site of a flowline transporting a fluid that includes dispersed oil in water. A sample of the fluid flowed through the flowline is obtained. The sample includes the oil phase and the water phase. The sample is combined with a chemical element that can separate the oil phase in the sample from the water phase in the sample. The separated oil phase and the chemical element are transferred into a measurement cell. The chemical element is removed from the measurement cell. After the chemical element is removed from the measurement cell, a quantity of the oil phase in the sample in the measurement cell is determined by a capacitive measurement technique. The determined quantity of the oil phase in the sample is provided.

20 Claims, 2 Drawing Sheets

(56) References Cited

U.S. PATENT DOCUMENTS

| | | | |
|---|---|---|---|
| 4,034,219 A | 7/1977 | Louden et al. | |
| 4,157,247 A | 6/1979 | Collins, III et al. | |
| 4,466,946 A | 8/1984 | Goddin, Jr. et al. | |
| 4,581,134 A | 4/1986 | Richter, Jr. et al. | |
| 4,589,896 A | 5/1986 | Chen et al. | |
| 4,701,187 A | 10/1987 | Choe | |
| 4,717,407 A | 1/1988 | Choe et al. | |
| 4,797,550 A | 1/1989 | Nelson et al. | |
| 4,809,543 A * | 3/1989 | Baillie | G01N 21/534 73/61.48 |
| 5,035,065 A | 7/1991 | Parkinson | |
| 5,067,345 A | 11/1991 | Mougne | |
| 5,259,239 A | 11/1993 | Gaisford | |
| 5,294,553 A | 3/1994 | Kawahara | |
| 5,381,002 A | 1/1995 | Morrow et al. | |
| 5,401,300 A | 3/1995 | Lokhandwala et al. | |
| 5,407,466 A | 4/1995 | Lokhandwala et al. | |
| 5,407,467 A | 4/1995 | Lokhandwala et al. | |
| 5,529,694 A * | 6/1996 | Strickler | G01N 33/1833 422/89 |
| 5,632,803 A | 5/1997 | Stoner | |
| 5,837,032 A | 11/1998 | Moll et al. | |
| 6,179,900 B1 | 1/2001 | Behling et al. | |
| 6,361,582 B1 | 3/2002 | Pinnau et al. | |
| 6,614,242 B2 | 9/2003 | Matter et al. | |
| 6,656,249 B1 | 12/2003 | Buisnnan | |
| 6,896,717 B2 | 5/2005 | Pinnau et al. | |
| 7,469,188 B2 | 12/2008 | Wee | |
| 8,323,392 B2 | 12/2012 | Jones | |
| 8,722,003 B1 | 5/2014 | Avagliano et al. | |
| 8,828,121 B1 | 9/2014 | He et al. | |
| 9,157,035 B1 | 10/2015 | Ball, IV et al. | |
| 9,181,499 B2 | 11/2015 | Mason et al. | |
| 9,244,017 B2 | 1/2016 | Cadieux et al. | |
| 9,448,221 B2 | 9/2016 | Duval et al. | |
| 10,024,835 B2 | 7/2018 | Sreekumar | |
| 10,197,545 B2 | 2/2019 | Sreekumar et al. | |
| 10,386,284 B2 | 8/2019 | Zhang | |
| 2005/0217479 A1 | 10/2005 | Hale et al. | |
| 2010/0264014 A1 | 10/2010 | Mignon et al. | |
| 2012/0111051 A1 | 5/2012 | Kulkarni et al. | |
| 2012/0168154 A1 | 7/2012 | Chinn et al. | |
| 2012/0323059 A1 | 12/2012 | Liu et al. | |
| 2013/0110411 A1 | 5/2013 | Black et al. | |
| 2015/0240717 A1 | 8/2015 | Starcher et al. | |
| 2015/0290575 A1 | 10/2015 | Rothermel et al. | |
| 2015/0298972 A1 | 10/2015 | Ballaguet et al. | |
| 2016/0121258 A1 | 5/2016 | First | |
| 2016/0228813 A1 | 8/2016 | Schwartz | |
| 2017/0312682 A1 | 11/2017 | Keller | |
| 2017/0320736 A1 | 11/2017 | Voss et al. | |
| 2019/0227020 A1 | 7/2019 | Tamida et al. | |

FOREIGN PATENT DOCUMENTS

| | | | |
|---|---|---|---|
| EP | 0684066 | 11/1995 | |
| EP | 1462775 A1 * | 9/2004 | G01F 23/26 |
| EP | 2932248 | 2/2020 | |
| GB | 2336668 | 10/1999 | |
| JP | S56162001 | 12/1981 | |
| JP | 2001133450 | 5/2001 | |
| JP | 3764701 | 4/2006 | |
| WO | WO 2010133315 | 11/2010 | |
| WO | WO 2018129228 | 7/2018 | |
| WO | WO 2018236644 | 12/2018 | |
| WO | WO 2013068320 | 5/2019 | |

OTHER PUBLICATIONS

Amo et al., "Low-Quality Natural Gas Sulfur Removal/Recovery," Membrane Technology and Research, DOE Report DE-AC21-92MC28133-01, Jan. 29, 1998, 107 pages.

Aschoundong et al., "Silane Modification of Cellulose Acetate Dense Films as Materials for Acid Gas Removal Macromolecules," Macromolecules, vol. 46, No. 14, Jul. 9, 2013, 11 pages.

ASTM "D 3921-85: Standard test method for oil and grease and petroleum hydrocarbons in water," 1985 (reapproved 1990), ASTM International, 5 pages.

ASTM "D 7066-04, Standard test method for dimer/trimer of chlorotrifluoroethylene (S-316) recoverable oil and grease and nonpolar by Infared determination," 2007, 9 pages.

ASTM International, "D 4281-95: Standard test method for oil and grease (fluorocarbon extractable substances) by gravimetric determination," An American Standard, 1995, reapproved 2005, 6 pages.

Belov et al., "Gas transport and free volume in hexafluoropropylene polymers," Journal of Membrane Science, vol. 383, Nov. 2011, 8 pages.

Ben-Shebil, "Effect of heat of adsorption on the adsorptive drying of solvents at equilibrium in a packed bed of zeolite," Chemical Engineering Journal, vol. 74, Issue 3, Jul. 1999, 12 pages.

Bernardo et al., "Gas transport properties of Pebax/room temperature ionic liquid gel membranes" Separation and Purification Technology vol. 97, Sep. 2012, 13 pages.

Bhide et al., "Hybrid processes for the removal of acid gases from natural gas," Journal of Membrane Science, vol. 140, Issue 1, Mar. 4, 1998, 2 pages, Abstract Only.

Chatterjee et al., "Poly(ether urethane) and poly (ether urethane urea) membranes with high H2S/CH4 selectivity," Journal of Membrane Science, vol. 135, No. 99, Nov. 1997, 8 pages.

Cirne et al., "Methods for Determination of Oil and Grease Contents in Wastewater from the Petrolem Industry," Chemistry and Chemical Technology, vol. 10, No. 4, 2016, 8 pages.

EPA Method 413.1, "Oil and Grease (Gravimetric, Separatory Funnel Extraction," Issued in 1974, Editorial revision 1978, Standard test method for oil and grease using gravimetric determination, 3 pages.

EPA Method 413.2, "Oil and Grease (Spectrophotometric, Infrared)," Issued in 1974, Editorial revision 1978, Standard test method for Oil and grease analysis using Freon extraction and IR absorbance without the Freon extract being treated by silica gel, 3 pages.

EPA, "Method 1664, Revision B: n-Hexane Extractable Material (HEM; Oil and Grease) and Silica Gel Treated n-Hexane Extractable Material (SGT-HEM; Non-polar Material) by Extraction and Gravimetry," United States Environmental Protection, Office of Water Agency, Feb. 2010, 35 pages.

EPA, "Oil And Grease (Gravimetric, Separatory Funnel Extraction)," EPA Method 418.1 (Issued in 1978), 3 pages.

Gabrus et al., "Experimental studies on 3 A and 4 A zeolite molecular sieves regeneration in TSA process: Aliphatic alcohols dewatering-water desorption," Chemical Engineering Journal, vol. 259, Jan. 2015, 11 pages.

Glasoe et al, "Solubility of water and deuterium oxide in carbon tetrachloride, toluene, and cyclohexane at various temperatures," Journal of Chemical & Engineering Data, 17(1), pp. 66-68, 1972, 3 pages.

Hibbard and Schalla, "NACA Research Memorandum: Solubility of Water in Hydrocarbons," National Advisory Committee for Aeronautics, Washington, Jul. 10, 1952, 27 pages.

International Standard, "ISO 5667-3: Water quality—sampling—part 3: guidance on the preservation and handling of water samples," 3rd edn, Dec. 15, 2003, 38 pages.

International Standard, "ISO 9377-2: Water quality—determination of hydrocarbon oil index—Part 2: Method using solvent extraction and gas chromatography," First edition, Oct. 15, 2000, 24 pages.

IP 426/98, "Determination of the oil content of effluent water—extraction and infra-red spectrometric method," Oil in Water, IP 426, 2012, 5 pages.

Jansen et al., "On the unusual solvent and the effect on the gas transport in perfluorinated Hyflon AD Membranes," Journal of Membrane Science, vol. 287, Issue 1, Jan. 2007, 6 pages.

Johnson et al, "The Molecular Complexity of Water in Organic Solvents Part II," J. Chem. Soc. A, Inorganic Phys. Theoretical, pp. 77-78, 1966, 2 pages.

Kirchnerová et al, "The Solubility of Water in Low-Dielectric Solvents," Can. J. Chem 54(24), pp. 3909-3916, Aug. 26, 1976, 8 pages.

(56) References Cited

OTHER PUBLICATIONS

Knauss et al, "The solubility of p-xylene in water as a function of temperature and pressure and calculated thermodynamic quantities," Geochimica et Cosmochimica Acta vol. 59, Issue 12, Jun. 1995, pp. 2443-2448, Mar. 1995, 6 pages.
Ko et al., "Analysis of purge gas temperature in cyclic TSA process," Chemical Engineering Science, vol. 57, Issue 1, Jan. 2002, 17 pages.
Kraftschik et al., "Dense film polyimide membranes for aggressive sour gas feed separations," Journal of Membrane Science vol. 428, Feb. 1, 2013, 12 pages.
Lallemand et al., "Extending the treatment of highly sour gases: cryogenic distillation," Digital Refining: Processing, Operations & Maintenance, Jan. 2014, 8 pages.
Lallemand et al., "Highly sour gas processing: Bulk removal with SPREX Process," IPTC-10581-MS, International Petroleum Technology Conference, Nov. 2005, 18 pages.
Lallemand et al., "Solutions for the treatment of highly sour gases," Digital Refinding: Processsing, Operations & Maintenance, Apr. 2012, 14 pages.
Lockhart, "Sour oil and gas management: 3.3," Volume Lii/New Developments: Energy, Transport, Sustainability Encyclopedia of Hydrocarbons, 2007, 34 pages.
Lokhandwala et al., "Membrane separation of nitrogen from natural gas: A case study from membrane synthesis to commerical deployment," Journal of Membrane Science 346, Jan. 2010, 10 pages.
Merkel and Toy, "Comparison of Hydrogen Sulfide Transport Properties in Fluorinated and Nonfluorinated Polymers," Macromolecules, vol. 39, No. 22, Sep. 2006, 10 pages.
Michell Instruments, "Impedance," Impedance Products, URL: <http://www.michell.com/uk/technology/impedence.htm> retrieved Sep. 9, 2019, 2 pages.
Odberg et al, "Studies of water in organic solvents using NMR and partition techniques-II Di-isopropyl ether, dibutyl phthalate and chloroform," Journal of Inorganic and Nuclear Chemistry vol. 34, Issue 8, Aug. 1972, pp. 2605-2616, Mar. 18, 1971, 12 pages..
Robeson, "The upper bound revisited," Journal of Membrane Science, vol. 320, Jul. 15, 2008, 11 pages.
Rufford et al., "The removal of CO2 and N2 from natural gas: A review of conventional and emerging process technologies," Journal of Petroleum Science and Engineering, vol. 94-95, Sep. 2012, 32 pages.
Sensorland.com, "Impedance Moisture Sensor Technology," How Sensors work—Moisture Sensors, URL: <http://www.sensorland.com/HowPage029.html> retrieved Sep. 9, 2019, 2 pages.
Simo et al., "Adsorption/Desorption of Water and Ethanol on 3 A Zeolite in Near-Adiabatic Fixed Bed," Ind. Eng. Chem. Res. 48, 20, Sep. 2009, 14 pages.
Vaisala, "Vaisala HUMICAP Sensor for Measuring Moisture in Oil," Technology Description, URL: <https://www.vaisala.com/sites/default/files/documents/HUMICAP-for-Moisture-in-oil-B211231EN-A.pdf> 2012, 2 pages.
Yang "Chapter 2: Measurement of Oil in Produced Water" in "Produced water" ed. K. Lee and J. Neff, pp. 57-88, Springer 2011, ISBN 978-1-4614-0045-5, 32 pages.
PCT International Search Report and Written Opinion in International Appln. No. PCT/US2021/043633, dated Nov. 5, 2021, 14 pages.

* cited by examiner

ONLINE MEASUREMENT OF DISPERSED OIL PHASE IN PRODUCED WATER

TECHNICAL FIELD

This application relates to flowlines carrying fluids, for example, fluids produced from subsurface reservoirs through wellbores.

BACKGROUND

Different types of fluids can be entrapped in subsurface reservoirs. The fluids can include hydrocarbons, for example, petroleum, crude oil, water, natural gas or mixtures of them. Such fluids can be produced, that is, raised to a surface of the Earth from the subsurface reservoirs through wellbores formed from the surface to the subsurface reservoirs. The fluids rise to the surface under the pressure of the subterranean zone in which the subsurface reservoirs reside or can be raised using secondary or tertiary production techniques. The produced fluids can include multiple phases, for example, an oil phase, a water phase, a gas phase, or a combination of any two or all three of them. For example, water produced through the wellbore can include hydrocarbons dispersed in the water in the form of emulsions. The produced water can satisfy use conditions for certain industrial applications if a quantity of the oil phase in the produced water is below a certain threshold.

SUMMARY

This specification describes technologies relating to online measurement of dispersed oil phase in produced water.

Certain implementations of the subject matter described here can be implemented as a method on-site of a flowline transporting a fluid that includes an oil phase and a water phase, for example, dispersed oil in water. A sample of the fluid flowed through the flowline is obtained. The sample includes the oil phase and the water phase. For example, the sample is drawn from the water phase and includes dispersed oil. The sample is combined with a chemical element that can separate the oil phase in the sample from the water phase in the sample. The separated oil phase and the chemical element are transferred into a measurement cell. The chemical element is removed from the measurement cell. After the chemical element is removed from the measurement cell, a quantity of the oil phase in the sample in the measurement cell is determined by a capacitive measurement technique. The determined quantity of the oil phase in the sample is provided.

An aspect combinable with any of the other aspects includes the following features. The sample is obtained by drawing the sample directly from the flowline into a sample cell fluidically coupled to the flowline.

An aspect combinable with any of the other aspects includes the following features. The chemical element is dry n-hexane.

An aspect combinable with any of the other aspects includes the following features. To combine the sample with dry n-hexane, the sample is mixed with the dry n-hexane by bubbling with dry gas.

An aspect combinable with any of the other aspects includes the following features. The separated water phase is transferred to a sample recovery cell separate from the measurement cell.

An aspect combinable with any of the other aspects includes the following features. An outlet of the sample cell is fluidically coupled to an inlet of the sample recovery cell through a first flow pathway of a three-way micro-valve. The outlet of the sample cell is fluidically coupled to an inlet of the measurement cell through a second flow pathway of the three-way micro-valve which is fluidically isolated from the first flow pathway of the three-way micro-valve. With the second flow pathway closed, the separated water phase is flowed through the first flow pathway in the three-way micro-valve from the outlet of the sample cell to the inlet of the sample recovery cell. At the outlet of the sample cell, the presence of the chemical element is detected. In response to detecting the presence of the chemical element at the outlet of the sample, the first flow pathway is closed and the second flow pathway is opened to flow the separated oil phase and the chemical element to the measurement cell.

An aspect combinable with any of the other aspects includes the following features. To detect the presence of the chemical element at the outlet of the sample cell, an electrical resistance of fluid flowed through the three-way micro-valve is measured. An increase in electrical resistance indicates a transition from presence of the separated water phase to presence of the chemical element.

An aspect combinable with any of the other aspects includes the following features. Detecting, at the outlet of the sample cell, the presence of the chemical element includes measuring a dielectric constant of fluid flowed through the three-way micro-valve. A decrease in the dielectric constant indicates a transition from presence of the separated water phase to presence of the chemical element.

An aspect combinable with any of the other aspects includes the following features. The separated water phase is flowed to the flowline.

An aspect combinable with any of the other aspects includes the following features. The oil phase in the sample is separated from the water phase in the sample by maintaining the sample cell in which the sample is combined with the chemical element at a temperature of 25° C.

An aspect combinable with any of the other aspects includes the following features. To remove the chemical element from the measurement cell, the separated oil phase and the chemical element in the measurement cell are boiled. The boiling removes the chemical element from the measurement cell.

An aspect combinable with any of the other aspects includes the following features. To determine the quantity of the oil phase in the sample in the measurement cell by capacitive measurement technique, an electrical excitation is applied to the oil phase from which the chemical element has been removed. A capacitance of the oil phase to which the electrical excitation has been applied varies until an entirety of the chemical element has been removed. After the capacitance of the oil phase stabilizes, a level of the oil phase is measured.

An aspect combinable with any of the other aspects includes the following features. After measuring the level of the oil phase, a fluid is injected through the measurement cell to purge the measurement cell of the separated oil phase and the chemical element.

Certain aspects of the subject matter described here can be implemented as a system implemented on-site of a flowline transporting a fluid that includes an oil phase and a water phase. The system includes a fluid sampling system configured to fluidically couple to the flowline. The fluid sampling system is configured to obtain a sample of the fluid flowed through the flowline. The sample includes the oil phase and the water phase. The system includes a sample cell fluidically coupled to the fluid sampling system. The sample cell is configured to receive the sample within an internal volume defined by the sample cell and receive a chemical element within the internal volume. When mixed with the sample, the chemical element is configured to separate the oil phase in the sample from the water phase in the sample. The system includes a measurement cell fluidically coupled to the sample cell. The measurement cell is configured to receive the separated oil phase and the chemical element from the sample cell, and remove the chemical element. The system includes a capacitive measurement system connected to the measurement cell. The capacitive measurement system is configured to implement a capacitive measurement technique to determine a quantity of oil in the separated oil phase in the measurement cell. The system includes one or more flow control devices fluidically coupled to each of the fluid sampling system, the sample cell and the measurement cell. The one or more flow control devices are configured to flow fluids through the system.

An aspect combinable with any of the other aspects includes the following features. The system includes a sample recovery cell separate from the measurement cell to which the separated water phase is transferred. The one or more flow control devices includes a three-way micro-valve fluidically coupled to an inlet of the sample recovery cell through a first flow pathway and an inlet of the measurement cell through a second flow pathway. The system includes a controller connected to the three-way micro-valve. The controller is configured to cause the three-way micro-valve to close the second flow pathway and open the first flow pathway to flow the separated water phase from the outlet of the sample cell to the inlet of the sample recovery cell through the first flow pathway. The controller is configured to detect, at the outlet of the sample cell, the presence of the chemical element. In response to detecting the presence of the chemical element at the outlet of the sample cell, the controller is configured to close the first flow pathway and open the second flow pathway to flow the separated oil phase and the chemical element to the measurement cell through the second flow pathway.

An aspect combinable with any of the other aspects includes the following features. To detect, at the outlet of the sample cell, the presence of the chemical element, the controller is configured to measure an electrical resistance of fluid flowed through the three-way micro-valve. An increase in the electrical resistance indicates a transition from presence of the separated water phase to presence of the chemical element.

An aspect combinable with any of the other aspects includes the following features. To detect, at the outlet of the sample cell, the presence of the chemical element, the controller is configured to measure a dielectric constant of fluid flowed through the three-way micro-valve. A decrease in the dielectric constant indicates a transition from presence of the separated water phase to presence of the chemical element.

An aspect combinable with any of the other aspects includes the following features. The measurement cell includes electrical heaters mounted within the measurement cell. The electrical heaters are configured to boil the separated oil phase and the chemical element within the measurement cell to remove the chemical element.

An aspect combinable with any of the other aspects includes the following features. The measurement cell includes an outlet. The capacitive measurement system includes a pair of electrodes disposed on either side of the outlet. The pair of electrodes can apply an electrical excitation to the oil phase from which the chemical element has been removed. A capacitance of the oil phase to which the electrical excitation has been applied varies until an entirety of the chemical element has been removed. Then, the capacitance stabilizes.

An aspect combinable with any of the other aspects includes the following features. A water-oil separator is fluidically coupled to the outlet of the measurement chamber. The one or more flow control devices flow fluid within the measurement cell to the water-oil separator.

An aspect combinable with any of the other aspects includes the following features. The one or more flow control devices include a naphtha injection pump fluidically connected to the measurement cell and configured to inject naphtha into the measurement cell to flow the fluid within the measurement cell to the water-oil separator.

Certain aspects of the subject matter described here can be implemented as a system implemented on-site of a flowline transporting a fluid including an oil phase and a water phase. The system includes a fluid sampling system configured to fluidically couple to the flowline. The fluid sampling system is configured to obtain a sample of the fluid flowed through the flowline. The sample includes the oil phase and the water phase. The system includes a sample cell fluidically coupled to the fluid sampling system. The sample cell is configured to receive the sample and a chemical element configured to separate the oil phase and the water phase in the sample. The system includes a mixer positioned within the sample cell. The mixer is configured to mix the sample and the chemical element causing the oil phase and the water phase to separate from each other, the chemical element remaining with the separated oil phase. The system includes a measurement cell fluidically connected to the sample cell. The measurement cell is configured to receive the separated oil phase and the chemical element from the sample cell. The system includes a capacitive measurement system connected to the measurement cell. The capacitive measurement system is configured to implement a capacitive measurement technique to determine a quantity of the oil phase in the separated oil phase received from the sample cell. The system includes a control system that includes a controller and one or more flow control devices operatively coupled to the controller and fluidically coupled to each of the fluid sampling system, the sample cell and the measurement cell. The controller is configured to control the one or more flow control devices to flow fluids through the system.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Water produced from subsurface reservoirs has multiple applications for example, the injection in the subterranean zone to maintain reservoir pressure, recovery and injection in disposal wells or overboard discharge. Knowing a quantity of dispersed hydrocarbons, that is, the oil phase, in the produced water enables determining if the water is suitable for one or more of such applications. Oil phase content beyond certain thresholds can result in reduced injectivity of the disposal wells due to pores plugging. In case of overboard discharge, exceeding the thresholds can lead to severe damage to marine life and to the environment in general.

The oil phase in the produced water can be determined by obtaining a sample of the produced water and testing the sample in a laboratory, for example, by implementing the liquid/liquid partition-gravimetric method 5520B or the Environmental Protection Agency (EPA) method 1164A. Laser induced fluorescence (LIF) or ultraviolet induced fluorescence techniques can also be implemented to determine the oil phase in water.

The present disclosure describes an online and on-site technique to determine the quantity of the oil phase in produced water. The techniques described here implement volumetric measurement instead of gravimetric or fluorescence-based measurements. The techniques are described on-site where the flowline carrying the produced water is installed. The techniques are implemented online by obtaining a sample of produced water directly from the flowline, providing the produced sample directly to a measurement system (described later), and providing the determined oil phase quantity as an output of the measurement system. Consequently, the need to transport the sample to a laboratory or to set up an extensive laboratory on-site is negated. Also, a quantity of the produced water sample is decreased. In addition, the measurement system can continuously determine the quantity of oil phase in multiple samples of produced water obtained over a period of time, and can generate a profile showing the quantity of the oil phase in the produced water over that period. Moreover, the use of the volumetric technique offers advantages over fluorescence-based techniques in which continuous cleaning of the measurement system is needed. Implementing the techniques described here can provide an accurate assessment of the most relevant fraction of oil in water by overcoming the limitations of other measurement principles, for example, ultraviolet or infrared-based measurement, and by overcoming the inability to differentiate aromatic measurement elements, which are harmless to injectivity, from aliphatic measurement elements, which are not soluble in water and cause great concern when injected. The techniques described here can be implemented continuously and in real-time to provide oil content in produced water content measurements which can alert operators on changes in the produced water outlet streams and to enable appropriate changes in the process operation, or to alert operators of any malfunction of upstream equipment. Implementing the subject matter described here enables monitoring water quality after any process to remove oil, signaling replacement of cartridge or membrane removing oil and providing monitoring to minimize hydrocarbon losses with water.

The measurement techniques described here include the following steps. A sample of produced water is drawn by means of an insertion probe from a flowline transporting a well homogenized mixture (for example, by using a static mixer, shear valve, or similar). The sample is then transferred to the measurement cell using electro passivated tubing to preserve the integrity of the sample. The sample includes a water phase and an oil phase. The sample is mixed with a chemical element (for example, n-hexane, specifically, dry n-hexane) which separates the oil phase from the water phase, resulting in two immiscible fluids. The chemical element is attached to the oil phase, which is lighter than the water phase. The oil phase and the chemical element are separated from the water phase. The chemical element is then separated from the oil phase, for example, by evaporation or boiling. The quantity of the oil phase is then determined by capacitive measurement techniques. By combining the quantity of the oil phase with the quantity of the sample that was drawn from the flowline, a measure of oil in water in the sample is determined.

Figure 1:
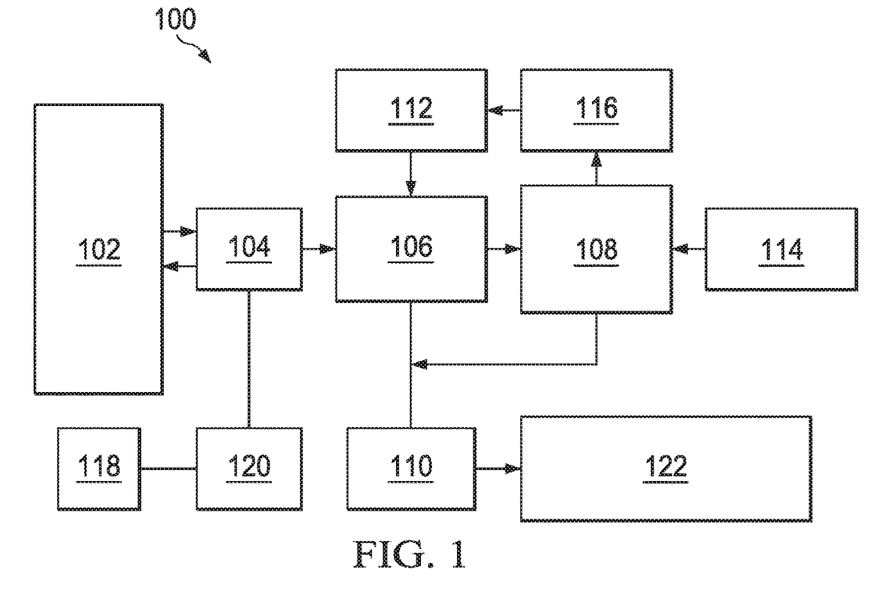
FIG. 1 is a schematic diagram of a system for online measurement of oil phase in produced water flowed through a flowline.

FIG. 1 is a schematic diagram of a system 100 for online measurement of oil phase in produced water flowed through a flowline 102. The system 100 is implemented on-site of the flowline 102 transporting a fluid that includes an oil phase and a water phase. For example, the fluid is produced water received from a wellbore. In some instances, the produced water can be transported to a gas-oil separation plant (GOSP) for processing, to another location at the well site for the injection, for disposal above the surface of the Earth, or for other applications. The fluid in the flowline 102 is a multi-phase fluid that includes an oil phase and a water phase. The system 100 can be fluidically coupled to the flowline 102 to draw measured samples of the fluid for the purposes described here. The sample drawn from the flowline 102 also includes the oil phase and the water phase. The ratio of the oil phase and the water phase in the sample is substantially equal to the ratio of the oil phase and the water phase in the fluid in the flowline 102. By "substantially equal to," it is meant that a measurement of the ratio of the oil phase and the water phase in the sample is a nearly accurate measurement (for example, within a 5% variance) of the ratio of the oil phase and the water phase in the fluid in the flowline 102. To accomplish this purpose, the multi-phase fluid can be effectively homogenized (e.g. by using a static mixer, shear valve, or similar).

In some implementations, the system 100 includes a fluid sampling system 104 to obtain a sample of the fluid flow through the flowline 102. This is achieved by inserting a probe into flowline 102, in a location where the multi-phase fluid is homogenous. The sample is then transferred using electro passivated tubing to the measurement cell. As described earlier, the sample includes the oil phase and the water phase, similar to the oil phase and the water phase, respectively, in the fluid flow through the flowline 102. For example, the fluid sampling system 104 includes a fluid flow pathway (for example, one or more tubes) fluidically coupled to the flowline 102 by one or more flow valves or flow pumps or both. The flow valves and the flow pumps are operated to draw a known quantity of the fluid sample (for example, the produced water) from the flowline 102 through the one or more tubes. In some implementations, the fluid sampling system 104 can include fluid flow pathways to return the sample fluid to the flowline 102 without processing. In some implementations, the fluid sampling system 104 can continuously draw and return fluid samples from the flowline 102, without providing any sample for processing. When activated by a controller 118 (described later), the fluid sampling system 104 can transfer a sample of the fluid for processing.

In some implementations, the system 100 includes a sample cell 106 fluidically coupled to the fluid sampling system 104. The sample cell 106 can be a container or similar chamber that defines an internal volume that is sufficient to carry the quantity of sample drawn by the fluid sampling system 104 from the flowline 102. For example, the sample cell 106 can have a volume of around 1 liter. Assuming oil concentration in a range between 50 parts per million (ppm) and 100 ppm, volumetric measurements on a 1 liter sample can be done in the range between 0.05 milliliters (ml) and 1.2 ml, which is compatible with capacitive level assessment. The fluid sampling system 104 and the sample cell 106 can be fluidically connected by a flow pathway (for example, a tube). In some implementations, a valve can be disposed in the flow pathway that connects the fluid sampling system 104 and the sample cell 106. The valve can be connected to and controlled by the controller 118. When the valve is closed, fluid drawn by the fluid sampling system 104 from the flowline 102 can be reinjected into the flowline 102. When the valve is open, the fluid drawn by the fluid sampling system 104 can be flowed to the sample cell 106. The controller 118 can control the valve to open for a duration sufficient to draw a quantity of the fluid needed to perform the oil phase measurement described here.

In addition to the sample, the sample cell 106 can receive a chemical element within the internal volume defined by the sample cell 106. When mixed with the sample, the chemical element can separate the oil phase in the sample from the water phase in the sample. In some implementations, the chemical element is n-hexane. In general, any chemical that is incompatible with water, with the ability to solubilize crude oil and with a boiling point sufficiently lower than crude oil to enable boiling off, can be used. Examples include pentane, hexane and heptane.

Figure 2A:
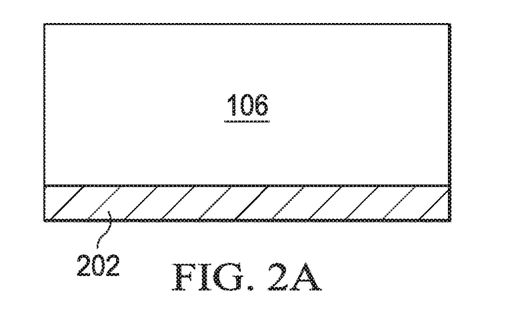
FIG. 2A is a schematic diagram of a sample cell of the system of FIG. 1 with a mixer.
Figure 2B:
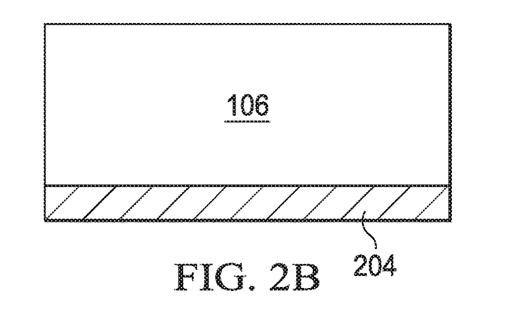
FIG. 2B is a schematic diagram of the sample cell of the system of FIG. 1 with a mixer.

In some implementations, the system 100 includes a mixer to mix the sample with the chemical element, for example, mix the produced water sample with the n-hexane. FIG. 2A is a schematic diagram of a sample cell 106 of the system of FIG. 1 with a mixer 202. In some implementations, the mixer 202 can be a mechanical mixer that resides within the sample cell 106 and, for example, is affixed to a bottom surface of the sample cell 106. The mixer 202 can include multiple blades that spin to mix the sample with the chemical element. The mixer 202 can be operatively connected to the controller 118, which can control operational parameters of the mixer 202, for example, a duration of mixing, a rate of spinning of the blades, and similar operational parameters. FIG. 2B is a schematic diagram of the sample cell 106 of the system of FIG. 1 with another mixer 204. In some implementations, the mixer 204 can be a bubbling mixer that includes a gas storage tank and a flow pathway (for example, a tube) that couples the gas storage tank to the internal volume of the sample cell 106. Gas from the gas storage tank can be flowed through the flow pathway to the internal volume of the sample cell 106 to mix the sample with the chemical element. The mixer 204 can be operatively connected to the controller 118, which can control operational parameters of the mixer 204, for example, opening or closing of the gas storage tank, a rate of flow of the gas, and similar operational parameters.

The controller 118 can operate the mixer (for example, the mixer 202, the mixer 204, or another mixer), for a duration sufficient for the phase separation of the oil phase and the water phase in the sample in the presence of n-hexane. In some implementations, the controller 118 can operate for a duration, ranging between 180 seconds and 600 seconds. In some implementations, the system described here can be operated without a mixer. In such implementations, sufficient duration is allowed for the oil to be solubilized by the solvent, that is, the n-hexane.

Mixing of the sample and the chemical element can be implemented by maintaining the sample cell 106 at a temperature, for example, 25° C. To do so, in some implementations, the system 100 includes a heater (not shown) operatively coupled to the sample cell 106. For example, the heater can include plates positioned within the internal volume of the sample cell 106 that can be electrically actuated to emit heat. A temperature sensor can be connected to the internal volume of the sample cell 106. The heater and the temperature sensor can be operatively connected to the controller 118, which can control the operation of the heater based on the temperature at which the internal volume of the sample cell 106 is to be maintained to facilitate the mixing of the sample in the chemical element.

In some implementations, the system 100 includes a chemical element storage tank 112 in which the chemical element, for example, the n-hexane, is stored. The chemical element storage tank 112 and the sample cell 106 can be fluidically coupled by a flow pathway (for example, a tube). In some implementations, a valve can be disposed in the flow pathway that connects the chemical element storage tank 112 and the sample cell 106. The valve can be connected to and controlled by the controller 118. When the valve is open, the chemical element flows from the chemical element storage tank 112 to the sample cell. When the valve is open, the flow of the chemical element to the sample cell 106 ceases. The controller 118 can control the valve to open for a duration sufficient to draw a quantity of the chemical element needed to mix with the quantity of the sample fluid such that the water phase and the oil phase can separate.

The quantity of n-hexane mixed with a unit volume of the sample to separate the oil phase and the water phase depends on a few factors. One is the oil solubility in the solvent. Another is the volume of solvent in relation to the volume of sample. In general, the quantity of solvent (that is, n-hexane) should be sufficient to ensure that all oil homogeneously dispersed in the sample is contacted and solubilized. In some implementations, the ratio of solvents versus sample is at least 10% (for example, between 10% and 15%). In some implementations, the ratio can be lower, for example, 8% or 7%.

In some implementations, the system 100 includes a measurement cell 108 fluidically coupled to the sample cell 106. The measurement cell 108 can receive the separated oil phase and the chemical element from the sample cell 106. In particular, the water phase is not flowed to the measurement cell 108. Within the measurement cell 108, the chemical element is removed. In some implementations, the system includes a sample recovery cell 110 separate from the measurement cell 108 to which the separated water phase is transferred. For example, each of the measurement cell 108 and the sample recovery cell 110 is a container or similar chamber that defines an internal volume that is sufficient to carry the quantity of separated oil phase and the chemical element or the separated water phase, respectively. Each of the measurement cell 108 and the sample recovery cell 110 can be fluidically connected to the sample cell 106 by a respective flow pathway (for example, a tube).

Figure 3:
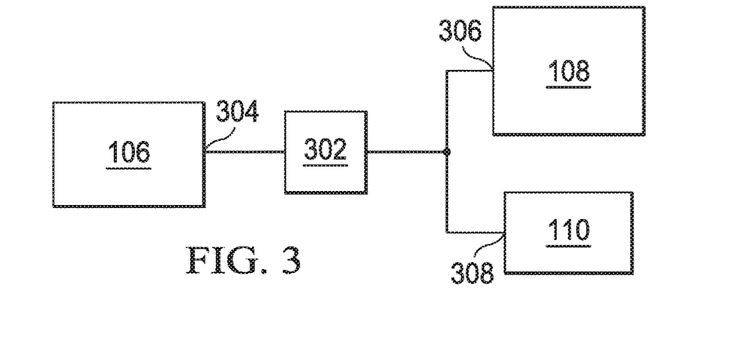
FIG. 3 is a schematic diagram of a three-way micro-valve fluidically coupling the sample cell, the measurement cell and a sample recovery cell of the system of FIG. 1.

Flow from the sample cell 106 to the measurement cell 108 or the sample recovery cell 110 can be controlled by a three-way micro-valve positioned in the flow pathways between the sample cell 106, the measurement cell 108, and the sample recovery cell 110. FIG. 3 is a schematic diagram of a three-way micro-valve 302 fluidically coupling the sample cell 106, the measurement cell 108 and a sample recovery cell 110 of the system 100. The micro-valve 302 couples an outlet 304 of the sample cell 106 to an inlet 306 of the measurement cell 108 through one fluid pathway, and couples the outlet 304 of the sample cell 106 to an inlet 308 of the sample recovery cell 110. At any given time, the micro-valve 302 can permit flow either from the outlet 304 of the sample cell 106 to the inlet 306 of the measurement cell 108 or from the outlet 304 of the sample cell 106 to the inlet 308 of the sample recovery cell 110, but not both. The micro-valve 302 is connected to the controller 118, which can control the opening and closing of the micro-valve 302 to implement the flows from the sample cell 106 to the measurement cell 108 or the sample cell 106 to the sample recovery cell 110.

As described earlier, when the oil phase and the water phase separate, the denser oil phase settles at the bottom of the sample cell 106. Consequently, the water phase first flows out of the outlet 304 of the sample cell 106. In some implementations, a pump or similar flow control device can be fluidically connected to the sample cell 106 to flow the fluid out of the sample cell 106 and into the measurement cell 108 or the sample recovery cell 110.

In some implementations, the system 100 includes one or more sensors (not shown) fluidically coupled to the outlet 304 of the sample cell 106 and the controller 118. When the fluid within the sample cell 106 flows out of the outlet 304, the one or more sensors can determine fluid properties of the fluid and transmit a signal representing the properties to the controller 118. For example, the one or more sensors can measure an electrical resistance (such as an inductive resistance) of the fluid that flows out of the outlet 304. In the produced water, the water phase is more conductive and has less electrical resistance compared to the combination of the oil phase and the n-hexane. As long as the one or more sensors measure an electrical resistance representative of the water phase, the controller 118 opens the flow pathway from the outlet 304 of the sample cell 106 to the inlet 308 of the sample recovery cell 110 and closes the flow pathway from the outlet 304 of the sample cell to the inlet 306 of the measurement cell 108. In response, the fluid in the sample cell 106 begins to flow from the sample cell 106 to the sample recovery cell 110 while avoiding the measurement cell 108. When all or most of the water phase has flowed out of the outlet 304, then the one or more sensors detect an increase in the electrical resistance as the combination of the oil phase and the n-hexane begins to flow from the outlet 304. In response to the one or more sensors detecting the increase in the electrical resistance, the controller closes the flow pathway from the outlet 304 of the sample cell to the inlet 308 of the sample recovery cell and opens the flow pathway from the outlet 304 of the sample cell 106 to the inlet 308 of the sample recovery cell 110.

In some implementations, the one or more sensors can measure a level, for example, a dielectric constant, of the fluid that flows out of the outlet 304. The dielectric constant of produced water (approximately 75) is higher than that of n-hexane (approximately 1.88). The one or more sensors can transmit the sensed dielectric constant to the controller 118, which can open and close the flow pathways to flow the water phase to the sample recovery cell 110 and the combination of the oil phase and the n-hexane to the measurement cell 108. In some implementations, any residual water in the fluid that flows out of the outlet 304 can be removed prior to the fluid flowing to the measurement cell 108 by passing the fluid through a molecular sieve (for example, the molecular sieve 116, described later). The molecular sieve absorbs the residual water and allows the remaining fluid to flow through.

Figure 4:
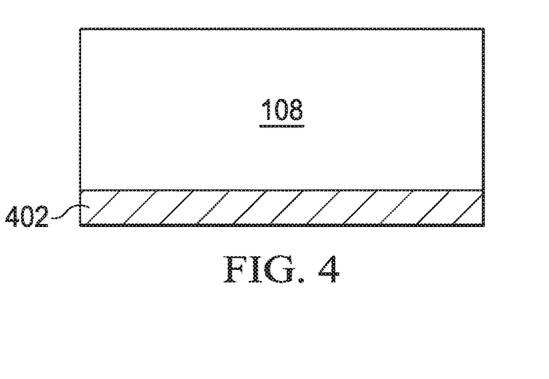
FIG. 4 is a schematic diagram of a measurement cell of the system of FIG. 1 with a heater.

After residual water has been removed from the combination of the oil phase and the chemical element (for example, the n-hexane) and the combination has flowed to the measurement cell 108, the chemical element can be separated from the oil phase. To do so, the combination of the oil phase and the chemical element is heated. FIG. 4 is a schematic diagram of the measurement cell 108 with a heater 402. In some implementations, the heater 402 includes electrical heaters mounted within the measurement cell 108. The electrical heaters can heat the combination of the oil phase at the chemical element within the measurement cell 108 to remove the chemical element. For example, the electrical heaters can be mounted to the walls of the measurement cell 108 and can heat the combination of the oil phase and the n-hexane to at least a temperature at which the n-hexane boils and evaporates (for example, at least 68° C.). Because the boiling point of the oil phase is greater than that of the n-hexane, only the n-hexane evaporates while the oil phase remains in the measurement cell 108. A duration for which the combination needs to be boiled depends on a quantity of the combination in the measurement cell 108.

In some implementations, the system 100 can recover the chemical element (for example, the n-hexane) that is separated from the oil phase by the boiling described earlier. For example, the system 100 can include a chemical element storage tank 112 (for example, n-hexane storage) that is fluidically connected to the measurement cell 108 by a fluid flow pathway with a valve controlled by the controller 118. During the boiling process described earlier, the controller 118 can cause the valve to be open to allow the separated chemical element to flow through the flow pathway for storage in the chemical element storage tank 112. In some implementations, cooling elements (for example, a heat exchanger, a Peltier type or similar cooling elements) can be positioned in the flow path of the chemical element so that the chemical element can be cooled (for example, to between 20-25° C.) before it reaches the chemical element storage tank 112. In some implementations, the system 100 can include a molecular sieve 116 (for example, a 3Angstrom protective cartridge) between the measurement cell 108 and the chemical element storage tank 112. The chemical element can be flowed through the molecular sieve 116 to remove any moisture from the chemical element. The moisture level need not be zero; a low level of moisture is acceptable. In some implementations, the system 100 includes a moisture analyzer to quantify a quantity of moisture in the recovered n-hexane.

Figure 5:
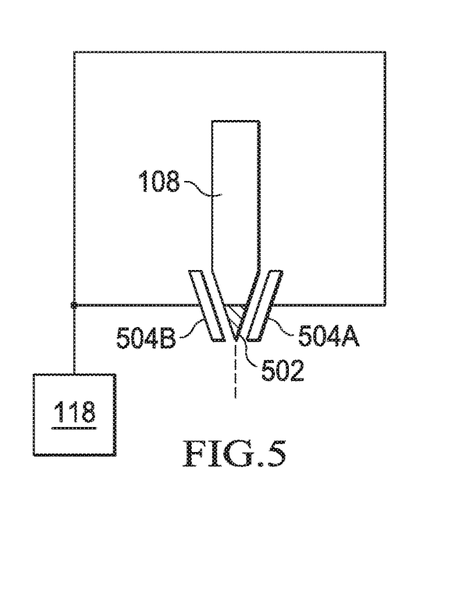
FIG. 5 is a schematic diagram of a capacitive measurement system of the system of FIG. 1.

In some implementations, a quantity of oil in the oil phase in the chemical or solvent that remains in the measurement cell 108 can be determined by implementing capacitive measurement techniques. FIG. 5 is a schematic diagram of a capacitive measurement system operatively connected to the measurement cell 108. The measurement cell 108 includes an outlet 502 at which the combination of the oil phase and the chemical element accumulates. The capacitive measurement system includes a pair of electrodes (a first electrode 504a, a second electrode 504b) disposed on either side of the outlet 502. While the electrical heater is heating the combination of the oil phase and the chemical element, the pair of electrodes can apply an electrical excitation (for example, a frequency of 10 kilo Hertz) to the combination at the outlet 502. As the chemical element boils off from the combination, its concentration in the combination decreases. Responsively, the capacitance of the oil phase varies. Once all of the chemical element has been boiled off or evaporated from the combination, only the oil phase remains and the capacitance stabilizes. The quantity of the oil in the remaining oil phase can then be determined from the stabilized capacitance value. In some implementations, the oil quantity can be determined by calibration of the system, by mapping the capacitance output at different levels (that is, volumes) of oil in the cell.

The controller 118 is operatively coupled to the pair of electrodes and is configured to transmit a control signal to cause the pair of electrodes to apply the electrical excitation at the outlet 502 of the measurement cell 108. In addition, the controller 118 is operatively coupled to a capacitor (not shown) that can measure the capacitance across the pair of electrodes. The controller 118 is also configured to compare capacitance values over the period of time to determine capacitance stabilization. For example, the controller 118 can determine that the capacitance values have stabilized when a difference between a greatest and least capacitance values measured by the capacitor over a pre-defined period of time is less than a threshold value.

In some implementations, the outlet 502 of the measurement cell 108 can be fluidically connected to the sample recovery cell 110. After the capacitance measurements described earlier, the oil phase can be flowed out of the measurement cell 108 through the outlet 502 and into the sample recovery cell 110. In some implementations, a valve can be disposed in the flow pathway that connects the outlet 502 of the measurement cell 108 and the sample recovery cell 110. The valve can be connected to and controlled by the controller 118. The controller 118 can control the valve to remain closed during the capacitance measurement described earlier, and to open after the capacitance measurement has been completed to allow the oil phase to flow through the outlet 502 to the sample recovery cell 110.

In some implementations, after the oil phase has been flowed out of the measurement cell 108, the internal volume of the measurement cell 108 can be cleaned. To do so, a naphtha storage tank 114 can be fluidically connected to the measurement cell 108 by a fluid flow pathway with a valve controlled by the controller 118. The controller 118 can cause naphtha from the naphtha storage tank 114 to be flowed into the measurement cell 108 to purge any residual contents in the measurement cell 108. After purging, the naphtha can be flowed to the sample recovery cell 110 through the outlet 502 of the measurement cell 108.

In some implementations, the system 100 includes a vessel 122 fluidically connected to an outlet of the sample recovery cell 110 by a fluid flow pathway with a valve controlled by the controller 118. The contents of the sample recovery cell 110 can be flowed to the vessel 122 for subsequent disposal. For example, the vessel 122 can be a water-oil separator (WOSEP), which is a produced water treatment unit found in oil and gas processing facilities. The contents of the sample recovery cell 110 are sent to the WOSEP because the contents are mostly composed of produced water and trace of crude oil, and the WOSEP is best suited to treat such a composition and ensure its removal from the produced water. Water in the WOSEP can be injected in the subterranean zone to maintain reservoir pressure or recovered and reinjected in disposal wells or discharged overboard. The techniques described here are implemented downstream of the WOSEP. Disposal streams are then sent back to the WOSEP to ensure removal of measured oil, naphtha used to clean the cell and slip hexane.

In some implementations, the system 100 includes one or more flow control devices 120 fluidically coupled to flow pathways throughout the system 100, for example, to each of the sample cell 106, the measurement cell 108, the sample recovery cell 110 and other components described earlier. The one or more flow control devices include pumps that can flow fluids through the system 100. In some implementations, flow through the system 100 can be implemented by creating pressure differentials that cause fluids to flow in the desired direction. For example, the n-hexane can be injected through a pump or the chemical element storage tank 112 can be pressurized with an inert and dry gas, for example, nitrogen. Fixed volume sampling loops can be used to control the volume fractions of the oil and water phases.

Figure 6:
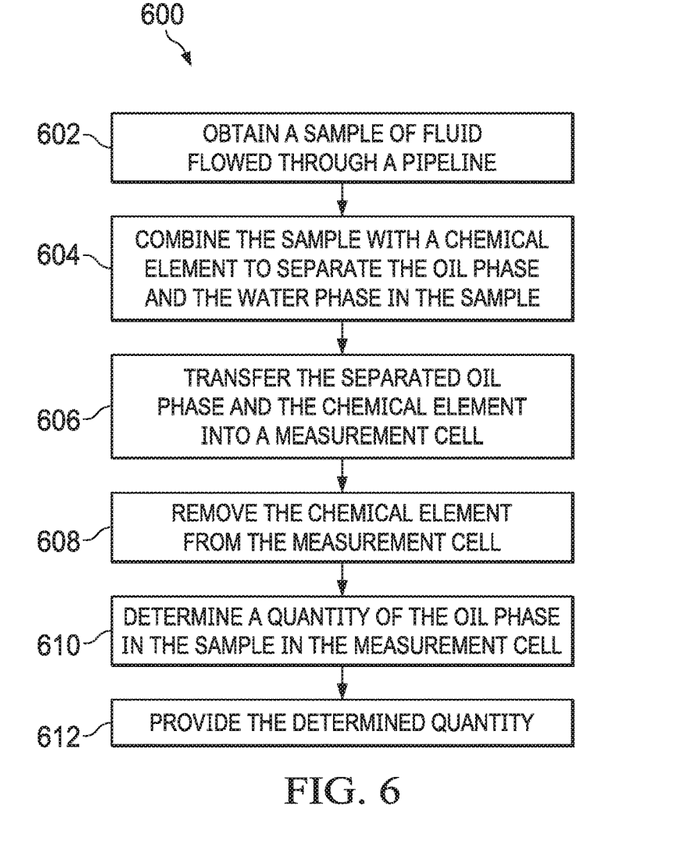
FIG. 6 is a flowchart of an example of a process implemented by the system of FIG. 1.

FIG. 6 is a flowchart of an example of a process 600 implemented by the system of FIG. 1. Some or all of the steps of the process 600 can be implemented by a controller, for example, the controller 118. In some implementations, the controller includes one or more processors and a computer-readable medium (for example, a non-transitory, computer-readable medium) storing instructions executable by the one or more processors to perform operations described with reference to the process 600 as well as those described generally in this disclosure. In some implementations, the controller can be implemented as software, firmware, hardware, processing circuitry, or any combination of them together with or independently of the one or more processors, and the computer-readable medium. As described earlier, the method can be implemented on-site of a flowline, for example, the flowline 102, transporting the fluid, for example, produced water, that includes an oil phase and a water phase.

At 602, a sample of the fluid flowed through the flowline is obtained. The sample includes the oil phase and the water phase, specifically, oil dispersed in water. For example, the controller 118 can control the fluid sampling system 104 to obtain a quantity of the sample from the flowline 102. At 604, the sample is combined with a chemical element configured to separate the oil phase in the sample from the water phase in the sample. For example, the controller 118 can flow the sample obtained by the fluid sampling system 104 to the sample cell 106. The controller 118 can flow n-hexane from the chemical element storage tank 112 into the sample cell 106. The controller 118 can operate a mixer (for example, the mixer 202 or the mixer 204). To mix the sample and the n-hexane. In some implementations, the controller 118 can operate the heater installed in the sample cell 106 to heat the internal volume of the sample cell during the mixing. As described earlier, mixing the sample with the n-hexane causes the oil phase and the water phase to separate. At 606, the separated oil phase and the chemical element are transferred into a measurement cell. For example, the controller 118 can flow the water phase from the sample cell 106 to the sample recovery cell 110, and flow the separated oil phase and the n-hexane from the sample cell 106 to the measurement cell 108. At 608, the chemical element is removed from the measurement cell. For example, the controller 118 can operate the electrical heaters installed in the measurement cell 108 to heat the combination of the oil phase and the n-hexane, thereby boiling off or evaporating the n-hexane out of the measurement cell 108. At 610, a quantity of the oil phase in the sample in the measurement cell 108 is determined. For example, the controller 118 can implement the capacitive measurement technique described earlier to determine the quantity of the oil phase in the sample that remains in the measurement cell 108 after the n-hexane has been removed from the measurement cell 108. At 612, the determined quantity is provided. For example, the controller 118 can include, or be operatively connected to a display device. The controller 118 can transmit the determined oil phase quantity to be displayed in the display device. Alternatively or in addition, the controller 118 can determine an oil in water quantity for the obtained sample. For example, if the quantity of sample obtained is one liter (1 L) and the quantity of oil phase in the sample is 50 µL, then the oil in water quantity for the sample is 50 µL divided by 1 L, which is 50 parts per million by volume (ppmv).

After the quantity of the oil phase has been determined, the oil phase and any remaining sample can be purged from the measurement cell 108 by a naphtha flow from the naphtha storage tank 114. The purged sample flows to the sample recovery cell 110 from which it can be flowed to the WOSEP 122. In some implementations, the measurement cell can be calibrated using a known amount of mineral oil and water, followed by the measurement of the remaining volume of the mineral oil after extraction and evaporation of the n-hexane, as described earlier. In some implementations, a mixer (not shown) can be implemented in the flowline 102 upstream of the sampling point at which the fluid sampling system 104 draws the sample. Doing so can ensure that the oil phase and the water phase ratio in the sample is representative of the corresponding ratio in the fluid flowed through the flowline 102. In some implementations, the flow pathways (that is, the tubes) through which the fluid sampling system 104 draws fluid from the flowline 102 can be treated (for example, an electro polish treatment or similar chemical treatment) to prevent water from adhering to the inner walls of the flow pathways.

In sum, the techniques described here implement a volumetric measurement cell that replaces equipment used in a gravimetric approach. The measurement cell does not need a glass window or similar transparent surface to induce and measure sample fluorescence, thereby avoiding the risk of fouling. Because the measurement system is online and on-site, and is fed by a side stream retrieved directly from the flowline, more than one measurement cell can be implemented in parallel. At every time instant, one cell can perform the measurement described earlier, one cell can be cleaned with a crude oil solvent, for example, naphtha or toluene, and one cell is in standby for redundancy. The measurement system described here can increase the measurement range from a few parts per million (ppm) to 100 ppm, to few ppm to percentage as the measurement cell of the measurement system can be designed to carry different volumes of the oil phase remaining after n-hexane evaporation. The evaporated n-hexane can be recovered, thereby reducing n-hexane consumption.

Thus, particular implementations of the subject matter have been described. Other implementations are within the scope of the following claims.

What is claimed is:

1. A method implemented on-site of a flowline transporting a fluid comprising an oil phase and a water phase, the method comprising:

obtaining a sample of the fluid flowed through the flowline, wherein the sample comprises the oil phase and the water phase;

combining the sample with a chemical element configured to separate the oil phase in the sample from the water phase in the sample;

transferring the separated oil phase and the chemical element into a measurement cell;

removing the chemical element from the measurement cell;

after removing the chemical element from the measurement cell, determining a quantity of the oil phase in the sample in the measurement cell by a capacitive measurement technique; and providing the determined quantity of the oil phase in the sample.

2. The method of claim 1, further comprising separating the oil phase in the sample from the water phase in the sample by maintaining the sample cell in which the sample is combined with the chemical element at a temperature of 25° C.

3. The method of claim 1, wherein removing the chemical element from the measurement cell comprises boiling the separated oil phase and the chemical element in the measurement cell, wherein the boiling removes the chemical element from the measurement cell.

4. The method of claim 1, wherein determining the quantity of the oil phase in the sample in the measurement cell by the capacitive measurement technique comprises:

applying an electrical excitation to the oil phase from which the chemical element has been removed, wherein a capacitance of the oil phase to which the electrical excitation has been applied varies until an entirety of the chemical element has been removed; and after the capacitance of the oil phase stabilizes, measuring a level of the oil phase.

5. The method of claim 4, further comprising, after measuring the level of the oil phase, injecting a fluid through the measurement cell to purge the measurement cell of the separated oil phase and the chemical element.

6. The method of claim 1, wherein the sample is obtained by drawing the sample directly from the flowline into a sample cell fluidically coupled to the flowline.

7. The method of claim 6, wherein the chemical element is dry n-hexane.

8. The method of claim 7, wherein combining the sample with dry n-hexane comprises mixing the sample with the dry n-hexane by bubbling with dry gas.

9. The method of claim 1, wherein the separated water phase is transferred to a sample recovery cell separate from the measurement cell.

10. The method of claim 9, further comprising:

fluidically coupling an outlet of the sample cell to an inlet of the sample recovery cell through a first flow pathway of a three-way micro-valve;

fluidically coupling the outlet of the sample cell to an inlet of the measurement cell through a second flow pathway of the three-way micro-valve which is fluidically isolated from the first flow pathway of the three-way micro-valve;

with the second flow pathway closed, flowing, through the first flow pathway in the three-way micro-valve, the separated water phase from the outlet of the sample cell to the inlet of the sample recovery cell;

detecting, at the outlet of the sample cell, the presence of the chemical element; and in response to detecting the presence of the chemical element at the outlet of the sample cell:
closing the first flow pathway; and
opening the second flow pathway to flow the separated oil phase and the chemical element to the measurement cell.

11. The method of claim 10, wherein detecting, at the outlet of the sample cell, the presence of the chemical element comprises measuring an electrical resistance of fluid flowed through the three-way micro-valve, wherein an increase in electrical resistance indicates a transition from presence of the separated water phase to presence of the chemical element.

12. The method of claim 10, wherein detecting, at the outlet of the sample cell, the presence of the chemical element comprises measuring a dielectric constant of fluid flowed through the three-way micro-valve, wherein a decrease in the dielectric constant indicates a transition from presence of the separated water phase to presence of the chemical element.

13. The method of claim 10, further comprising flowing the separated water phase to the flowline.

14. A system implemented on-site of a flowline transporting a fluid comprising an oil phase and a water phase, the system comprising:
a fluid sampling system configured to fluidically couple to the flowline, the fluid sampling system configured to obtain a sample of the fluid flowed through the flowline, wherein the sample comprises the oil phase and the water phase;
a sample cell fluidically coupled to the fluid sampling system, the sample cell configured to:
receive the sample within an internal volume defined by the sample cell, and
receive a chemical element within the internal volume defined by the sample cell, which, when mixed with the sample, is configured to separate the oil phase in the sample from the water phase in the sample;
a measurement cell fluidically coupled to the sample cell, wherein the measurement cell is configured to:
receive the separated oil phase and the chemical element from the sample cell, and
remove the chemical element; and
a capacitive measurement system connected to the measurement cell, the capacitive measurement system configured to implement a capacitive measurement technique to determine a quantity of oil in the separated oil phase in the measurement cell; and
one or more flow control devices fluidically coupled to each of the fluid sampling system, the sample cell and the measurement cell, the one or more flow control devices configured to flow fluids through the system.

15. The system of claim 14, wherein the measurement cell comprises electrical heaters mounted within the measurement cell, wherein the electrical heaters are configured to boil the separated oil phase and the chemical element within the measurement cell to remove the chemical element.

16. The system of claim 14, wherein the measurement cell comprises an outlet, wherein the capacitive measurement system comprises a pair of electrodes disposed on either side of the outlet, the pair of electrodes configured to apply an electrical excitation to the oil phase from which the chemical element has been removed, wherein a capacitance of the oil phase to which the electrical excitation has been applied varies until an entirety of the chemical element has been removed.

17. The system of claim 14, wherein the system comprises a sample recovery cell separate from the measurement cell to which the separated water phase is transferred,
wherein the one or more flow control devices includes a three-way micro-valve fluidically coupled to an inlet of the sample recovery cell through a first flow pathway and an inlet of the measurement cell through a second flow pathway, wherein the system comprises a controller connected to the three-way micro-valve, the controller is configured to:
cause the three-way micro-valve to:
close the second flow pathway, and
open the first flow pathway to flow the separated water phase from the outlet of the sample cell to the inlet of the sample recovery cell through the first flow pathway,
detect, at the outlet of the sample cell, the presence of the chemical element, and
in response to detecting the presence of the chemical element at the outlet of the sample cell, cause the three-way micro-valve to:
close the first flow pathway, and
open the second flow pathway to flow the separated oil phase and the chemical element to the measurement cell through the second flow pathway.

18. The system of claim 17, wherein, to detect, at the outlet of the sample cell, the presence of the chemical element, the controller is configured to measure an electrical resistance of fluid flowed through the three-way micro-valve, wherein an increase in the electrical resistance indicates a transition from presence of the separated water phase to presence of the chemical element.

19. The system of claim 17, wherein, to detect, at the outlet of the sample cell, the presence of the chemical element, the controller is configured to measure a dielectric constant of fluid flowed through the three-way micro-valve, wherein a decrease in the dielectric constant indicates a transition from presence of the separated water phase to presence of the chemical element.

20. A system implemented on-site of a flowline transporting a fluid comprising an oil phase and a water phase, the system comprising:
a fluid sampling system configured to fluidically couple to the flowline, the fluid sampling system configured to obtain a sample of the fluid flowed through the flowline, wherein the sample comprises the oil phase and the water phase;
a sample cell fluidically coupled to the fluid sampling system, the sample cell configured to receive the sample and a chemical element configured to separate the oil phase and the water phase in the sample;
a mixer positioned within the sample cell, the mixer configured to mix the sample and the chemical element causing the oil phase and the water phase to separate from each other, the chemical element remaining with the separated oil phase;
a measurement cell fluidically connected to the sample cell, the measurement cell configured to receive the separated oil phase and the chemical element from the sample cell;
a capacitive measurement system connected to the measurement cell, the capacitive measurement system configured to implement a capacitive measurement technique to determine a quantity of the oil phase in the separated oil phase received from the sample cell; and a control system comprising:
 a controller, and
 one or more flow control devices operatively coupled to the controller and fluidically coupled to each of the fluid sampling system, the sample cell and the measurement cell, the controller configured to control the one or more flow control devices to flow fluids through the system.

* * * * *